United States Patent
Smith (10) Patent No.: US 8,118,783 B2
(45) Date of Patent: Feb. 21, 2012

(54) ACCESS ASSEMBLY WITH SPHERICAL VALVE

(75) Inventor: Robert C. Smith, Middletown, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 428 days.

(21) Appl. No.: 12/332,391

(22) Filed: Dec. 11, 2008

(65) Prior Publication Data
US 2009/0192465 A1 Jul. 30, 2009

Related U.S. Application Data

(60) Provisional application No. 61/024,599, filed on Jan. 30, 2008.

(51) Int. Cl.
*A61M 5/178* (2006.01)
(52) U.S. Cl. ......... 604/164.04; 604/167.03; 604/167.04; 604/167.06
(58) Field of Classification Search ............. 604/164.04, 604/167.01–167.06; 606/167, 185
See application file for complete search history.

(56) References Cited

U.S. PATENT DOCUMENTS

| | | | |
|---|---|---|---|
| 4,874,378 A | 10/1989 | Hillstead | |
| 5,389,080 A | 2/1995 | Yoon | |
| 5,395,342 A | 3/1995 | Yoon | |
| 5,423,761 A | 6/1995 | Hein et al. | |
| 5,429,609 A | 7/1995 | Yoon | |
| 5,478,318 A | 12/1995 | Yoon | |
| 5,584,847 A | 12/1996 | Duluco et al. | |
| 5,613,954 A | 3/1997 | Nelson et al. | |
| 5,820,600 A | 10/1998 | Carlson et al. | |
| 5,865,817 A | 2/1999 | Moenning et al. | |
| 5,924,976 A | 7/1999 | Stelzer et al. | |
| 6,036,711 A | 3/2000 | Mozdzierz et al. | |
| 6,039,725 A | 3/2000 | Moenning et al. | |
| RE36,702 E | 5/2000 | Green et al. | |
| 6,086,603 A | 7/2000 | Termin et al. | |
| 6,162,196 A | 12/2000 | Hart et al. | |
| 6,309,345 B1 | 10/2001 | Stelzer et al. | |
| 6,832,984 B2 | 12/2004 | Stelzer et al. | |
| 7,186,265 B2 | 3/2007 | Sharkawy et al. | |
| 2004/0068232 A1 | 4/2004 | Hart et al. | |
| 2004/0204682 A1 | 10/2004 | Smith | |
| 2005/0212221 A1 | 9/2005 | Smith et al. | |
| 2006/0211992 A1 | 9/2006 | Prosek | |

(Continued)

FOREIGN PATENT DOCUMENTS

EP 0 638 290 A1 2/1995
(Continued)

OTHER PUBLICATIONS

European Search Report for Application No. EP 06005183, date of completion Jun. 29, 2006 (11 pgs.).

(Continued)

*Primary Examiner* — Jackie Ho
*Assistant Examiner* — Victoria P Campbell (57) ABSTRACT

A surgical portal apparatus includes a portal member dimensioned to access tissue and having a longitudinal passageway therethrough to permit access to underlying tissue, and defining leading and trailing ends, a seal housing associated with the portal member and a seal mount at least partially disposed within the seal housing. The seal mount is adapted for rotational movement within the seal housing. The seal mount includes an instrument seal adapted to establish a substantial sealed relation with a surgical object introduced within the longitudinal passageway and a closure valve adapted to substantially close the longitudinal passageway in the absence of the object.

9 Claims, 12 Drawing Sheets

U.S. PATENT DOCUMENTS

2006/0217666 A1    9/2006   Wenchell
2006/0224120 A1   10/2006   Smith

FOREIGN PATENT DOCUMENTS

| | | |
|---|---|---|
| EP | 1 707 133 | 10/2006 |
| EP | 1 707 133 A1 | 10/2006 |
| EP | 1 709 918 A1 | 10/2006 |
| EP | 2 042 114 | 4/2009 |
| WO | WO 0241795 | 5/2002 |
| WO | WO 03/094760 | 11/2003 |
| WO | 2008/045744 | 4/2008 |
| WO | 2008/093313 | 8/2008 |

OTHER PUBLICATIONS

European Search Report for Application No. EP 08253100, dated Dec. 12, 2008 (2 pgs).

International Search Report EP 09 25 0071 dated Jul. 7, 2010.

ACCESS ASSEMBLY WITH SPHERICAL VALVE

CROSS REFERENCE TO RELATED APPLICATION

The present application claims the benefit of and priority to U.S. Provisional Application Ser. No. 61/024,599 filed on Jan. 30, 2007, the entire contents of which are incorporated herein by reference.

TECHNICAL FIELD

The present disclosure relates to a valve system adapted to permit the introduction of surgical instrumentation into a patient's body. In particular, the present disclosure relates to a valve system for use with an introducer which is intended for insertion into a patient's body, and to receive an instrument in sealing engagement therewith.

DESCRIPTION OF THE RELATED ART

Minimally invasive and laparoscopic procedures generally require that any instrumentation inserted into the body is sealed, e.g., provisions may be made to ensure that gases and/or fluids do not enter or exit the body through an endoscopic incision, such as, for example in surgical procedures where the surgical region is insufflated. For such procedures, the introduction of a tube into anatomical cavities, such as the peritoneal cavity, is usually accomplished by use of a system incorporating a trocar and cannula assembly. Since the cannula is in direct communication with the interior of the peritoneal cavity, insertion of the cannula into an opening in the patient's body to reach the inner abdominal cavity may be adapted to maintain a fluid tight interface between the abdominal cavity and the outside atmosphere. In view of the desire to maintain the atmospheric integrity of the inner area of the cavity, a seal assembly for a cannula, which permits introduction of a wide range of surgical instrumentation and maintains the atmospheric integrity of the inner area of the cavity is desirable. In this regard, there have been a number of attempts in the prior art to achieve such sealing requirements. A difficulty encountered with conventional seal assemblies, however, is the inability of accommodating the wide range of sizes of instrumentation. In addition, angulation and/or manipulation of instrumentation within the cannula often present difficulties with respect to maintaining seal integrity.

SUMMARY

Accordingly, the present disclosure is directed to a surgical portal apparatus. The portal apparatus includes a portal member dimensioned to access tissue and having a longitudinal passageway therethrough to permit access to underlying tissue, and defining leading and trailing ends, a seal housing associated with the portal member and a seal mount at least partially disposed within the seal housing. The seal mount is adapted for rotational movement within the seal housing. The seal mount includes an instrument seal adapted to establish a substantial sealed relation with a surgical object introduced within the longitudinal passageway and a closure valve adapted to substantially close the longitudinal passageway in the absence of the object.

In another embodiment, the surgical portal apparatus includes a portal member dimensioned to access tissue and having proximal and distal ends, and a longitudinal passageway extending from the proximal end to the distal end to permit access to underlying tissue. The portal member has a seal housing disposed between the proximal and the distal ends and a seal mount at least partially disposed within the seal housing. The seal mount is adapted for rotational movement within the seal housing. The seal mount includes an object seal adapted to establish a substantial sealed relation with a surgical object introduced within the longitudinal passageway. The seal mount may include a closure valve adapted to substantially close the longitudinal passageway in the absence of the object. The closure valve may be disposed distal to the object seal or, alternatively, disposed proximal of the object seal. The seal housing may be disposed adjacent the distal end of the portal member. The seal mount may include a mount base to which the object seal is mounted. The mount base may define an internal taper adapted to generally direct the surgical object toward the object seal and in general alignment with the longitudinal axis.

The seal mount, the object seal and the closure valve may be monolithically formed.

The seal housing may define a portal anchor adapted to facilitate anchoring of the portal member relative to tissue. The portal anchor may define a generally bulbous configuration. The portal anchor may be adjacent the distal end of the portal member.

BRIEF DESCRIPTION OF THE DRAWINGS

The foregoing features of the present disclosure will become more readily apparent and will be better understood by referring to the following detailed description of embodiments, which are described hereinbelow with reference to the drawings wherein.

DETAILED DESCRIPTION

A surgical portal apparatus 2 of the present disclosure provides access to underlying body tissue and also provides a substantial seal between a body cavity of a patient and the outside atmosphere before, during and after insertion of an instrument. Moreover, the portal apparatus 2 of the present invention is capable of accommodating instruments of varying diameters, e.g., from 5 mm to 15 mm, by providing a gas tight seal with each instrument when inserted. The flexibility of the present surgical portal apparatus 2 greatly facilitates endoscopic surgery where a variety of instruments having different diameters are often needed during a single surgical procedure.

The portal apparatus 2 incorporates a seal adapted for the introduction and manipulation of various types of instrumentation while maintaining a fluid tight interface about the instrumentation to preserve the atmospheric integrity of a surgical procedure from gas and/or fluid leakage. Specifically, the seal accommodates angular manipulation of the surgical instrument relative to the seal axis. This feature of the present disclosure desirably minimizes the entry and exit of gases and/or fluids to/from the body cavity. Examples of instrumentation include clip appliers, graspers, dissectors, retractors, staplers, laser probes, photographic devices, endoscopes and laparoscopes, tubes, and the like. Such instruments will be collectively referred to herein as "instruments or instrumentation".

In the following description, as is traditional the term "proximal" refers to the portion of the instrument closest to the operator while the term "distal" refers to the portion of the instrument remote from the operator.

Referring now to the drawings, in which like reference numerals identify identical or substantially similar parts throughout the several views, FIGS. 1-4 illustrate the surgical portal apparatus 2 of the present disclosure. Portal apparatus 2 may be adapted for use as a cannula suitable for the intended purpose of accessing a body cavity, for example, the abdominal cavity, and permit introduction of instruments therethrough. As an alternate embodiment, portal apparatus 2 may be adapted to receive the hand and possibly the arm of the surgeon during a minimally invasive procedure where hand access is desired. Portal apparatus 2 is particularly adapted for use in laparoscopic surgery where the peritoneal cavity 72 is insufflated with suitable gas, e.g., $CO_2$, to raise the cavity wall 70 from the internal organs therein. Portal apparatus 2 is typically used with an obturator assembly (not shown) which is a sharp pointed instrument positionable within the passageway of the portal apparatus 2. The obturator assembly is utilized to penetrate the abdominal wall and then subsequently removed from the portal apparatus to permit introduction of the surgical instrumentation utilized to perform the procedure.

Portal apparatus 2 includes portal member 10 having proximal and distal ends 12, 14, respectively. Portal member 10 includes portal sleeve 16 and seal housing 20 mounted to proximal end 12 of the sleeve 16. Portal sleeve 16 defines a longitudinal axis "a" extending along the length of sleeve 16. Sleeve 16 further defines an internal longitudinal passage 18 dimensioned to permit passage of surgical instrumentation. Sleeve 16 may be formed of stainless steel or other rigid materials such as a polymeric material or the like. Sleeve 16 may be clear or opaque. The diameter of sleeve 16 may vary, but typically ranges from 10 to 15 mm for use with the seal housing 20 of the present disclosure.

Figure 1:
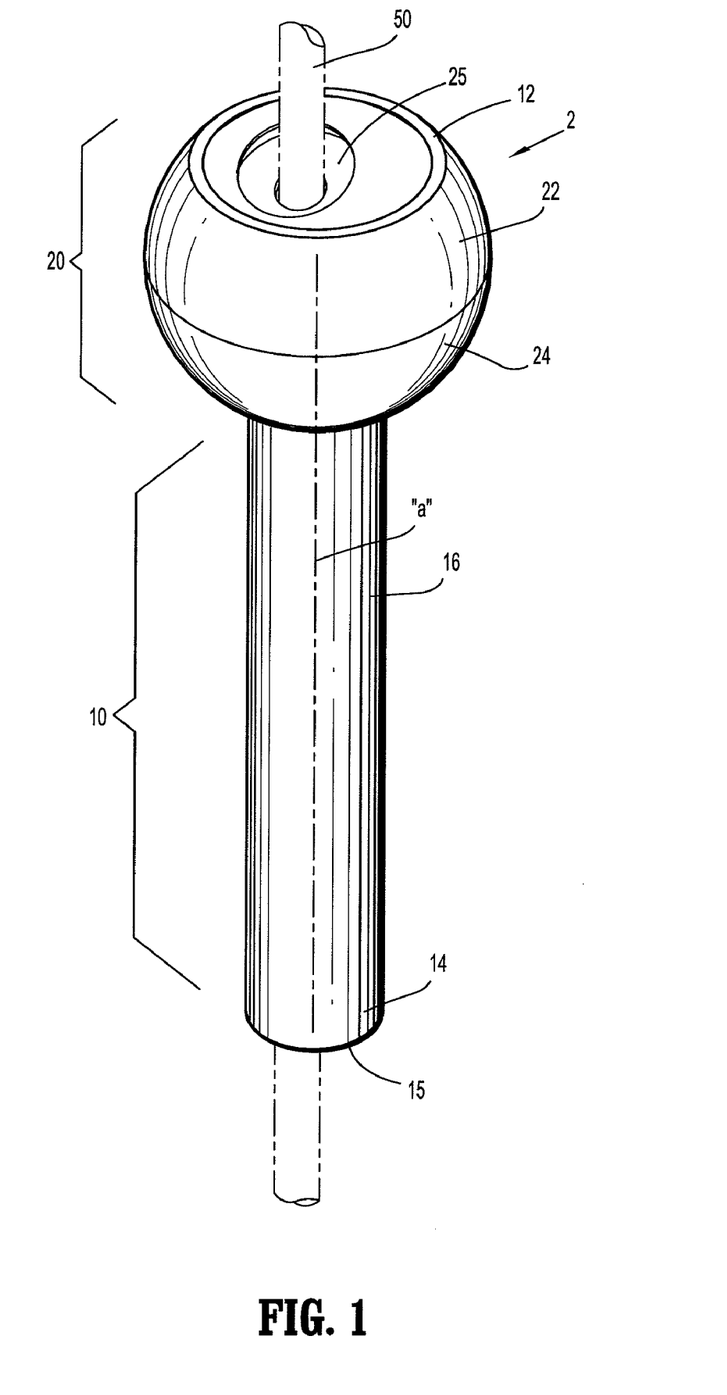
FIG. 1 is a perspective view of a surgical portal apparatus in accordance with the principles of the present disclosure.

Referring now to FIG. 1, seal housing 20 includes two components, namely, proximal housing component 22 and distal housing component 24. Distal housing component 24 is attached to the proximal end 12 of portal sleeve 16 by conventional means or may be integrally bound with the sleeve 16. Proximal housing component 22 is connectable to distal housing component 24 by any conventional means including a snap fit arrangement, threaded coupling, clamp coupling, bayonet coupling, etc. Seal housing 20 defines a generally spherical configuration.

Figure 2:
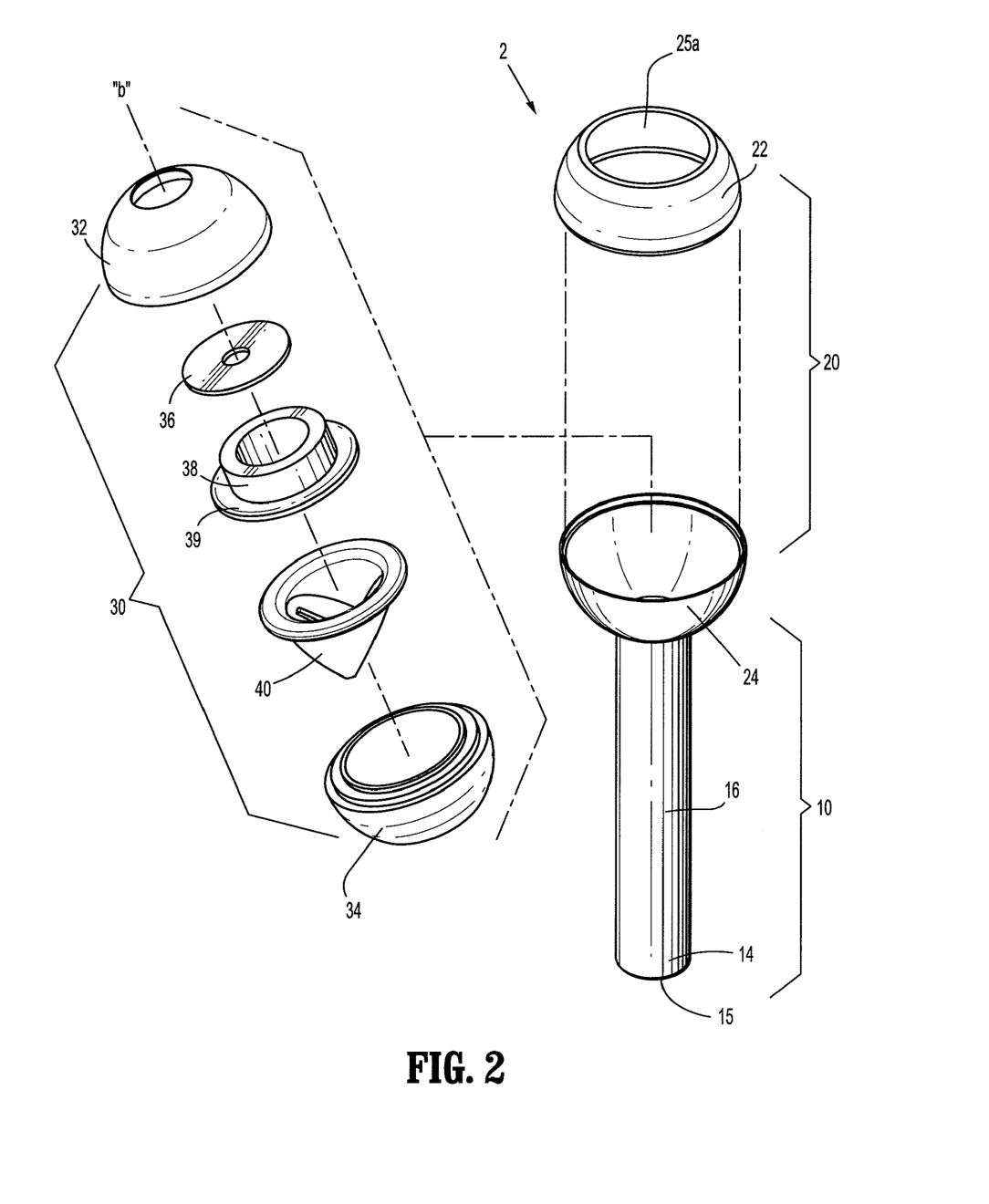
FIG. 2 is a perspective view with parts separated of the portal apparatus.
Figure 3:
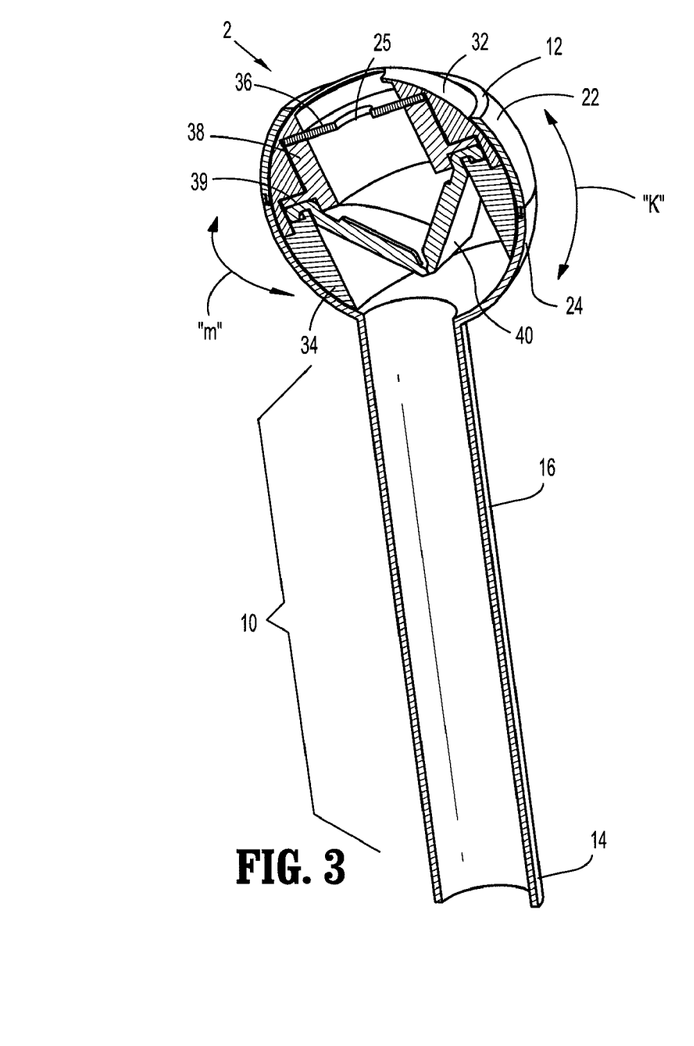
FIG. 3 is a perspective view in cross-section of the portal apparatus.
Figure 4:
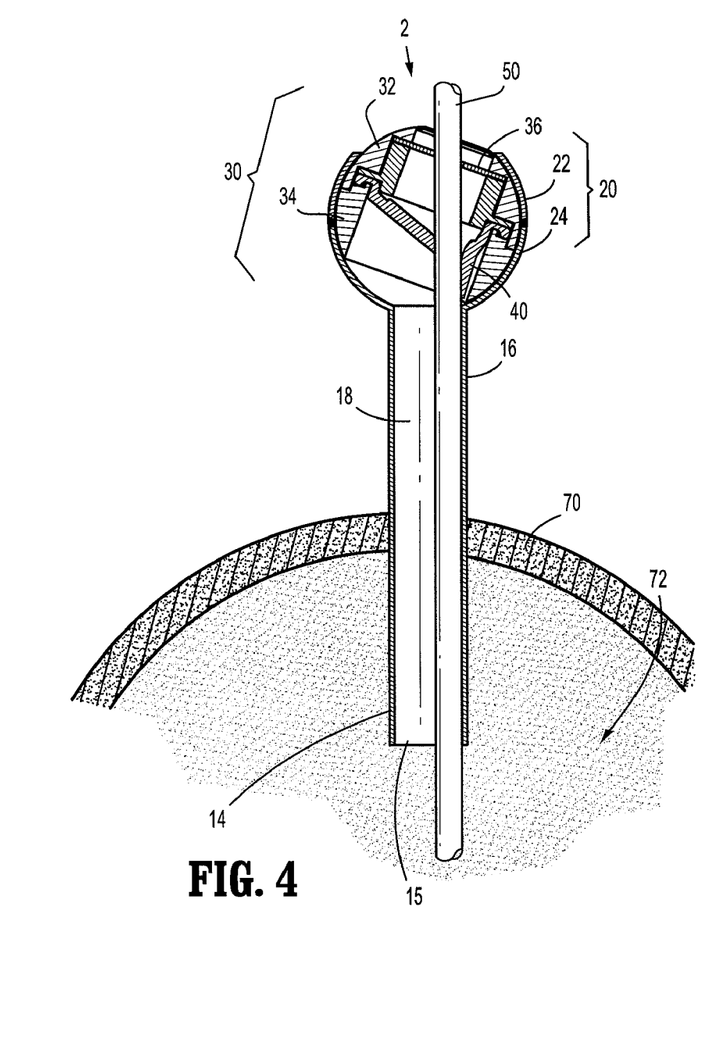
FIG. 4 is a side cross-sectional view of the portal apparatus accessing body tissue.

Referring now to FIGS. 2-4, portal apparatus further includes seal mount 30 which is disposed within seal housing 20. Seal mount 30 includes multiple components, namely, proximal seal mount component 32 which is connectable to distal seal mount component 34. Proximal and distal seal mount components 32, 34 may be connected via male-female lip connection, threaded type connection, etc.

When connected, proximal and distal seal mount components 32, 34 form a generally spherical outer wall that substantially conforms to the generally spherical inner walls of proximal and distal housing components 22, 24. Seal mount 30 further may include zero closure valve 40 and object seal 36.

With reference to FIG. 2, in conjunction with FIGS. 1 and 3-4, zero closure valve 40 may be a duck bill valve, which tapers distally and inwardly to a sealed configuration as shown in the figure. Valve 40 opens to permit passage of the surgical instrumentation and closes in the absence of the instrumentation. Valve 40 is adapted to close upon exposure to the forces exerted by the insufflation gases in the internal cavity. Other zero closure valves are also contemplated including single or multiple slit valve arrangements, trumpet valves, flapper valves, etc.

Object seal 36 may be constructed from rubber or any other elastomeric material contemplated in the art. Aperture 25 of the object seal 36 may vary in size depending on the types of instruments that are being utilized. Object seal 36 functions in minimizing the loss of insufflation gasses through portal member 10 by forming a substantial seal about the surgical object, e.g., surgical instrument.

Seal mount 30 further includes a mount base 38. Mount base 38 may be substantially cylindrical in shape, as shown in FIG. 2. In this configuration, object seal 36 may be mounted between the proximal rim of mount base 38 and internal transverse ledge of proximal seal mount component 32. Mount base 38 may include a flange 39. Flange 39 may be configured to engage the peripheral area of closure valve 40.

Referring again to FIGS. 1-4, use of the seal assembly 2 and portal member 10 in connection with introduction of a surgical instrument will be discussed. Portal member 10 is introduced into an insufflated abdominal cavity in a conventional manner such as, e.g., with the use of an obturator. The obturator is subsequently removed and a surgical instrument or object 50 is inserted into seal housing 20 through mount base 38 of seal mount 30. If the axis of the instrument 50 is not perfectly aligned with the aperture 25 of object seal 36, seal mount 30 will swivel, pivot or angulate within seal housing 20, thereby bringing aperture 25 into alignment with the surgical instrument 50.

As seen in FIG. 4, the instrument 50 passes further distally into seal mount 30 passing through the zero closure valve 40 and portal sleeve 16 and into the body cavity 72. As the instrument 50 passes distally, seal mount 30 is free to swivel further with respect to portal member 10. In addition, as the surgeon manipulates the instrument within the body cavity, seal mount 20 including object seal 36 and zero closure valve 40 is able to spherically rotate therein. For example, the seal mount 20 may rotate about seal axis "b" in the direction of arrows "m" (FIG. 3) and/or pivot in the direction of arrows "k" (FIG. 3) relative to the seal axis "b", thereby assisting object seal 36 in maintaining sealing engagement with the instrument passed therethrough.

Figure 5:
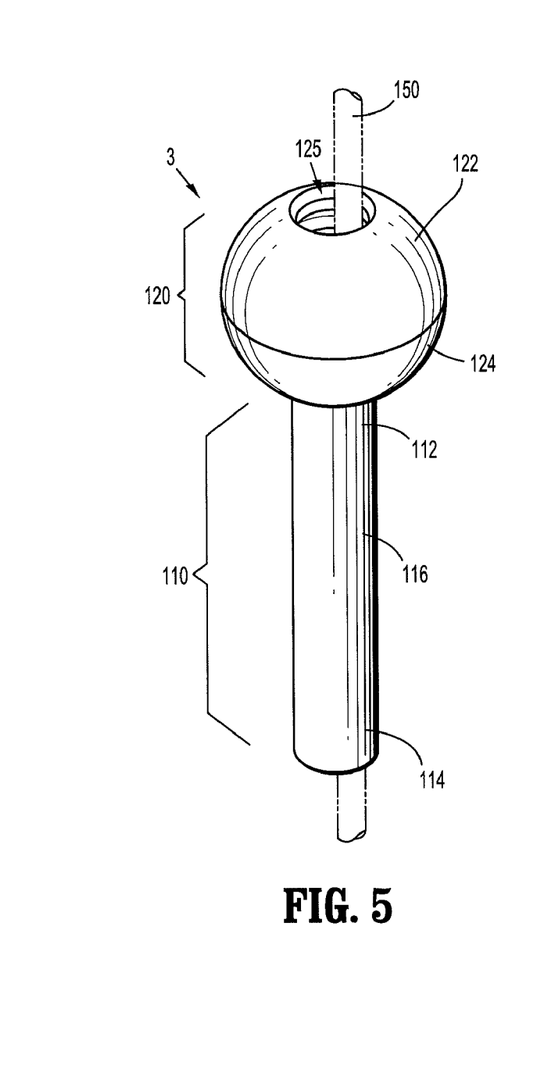
FIG. 5 is a perspective view of an alternate embodiment of the portal apparatus of FIG. 1.
Figure 6:
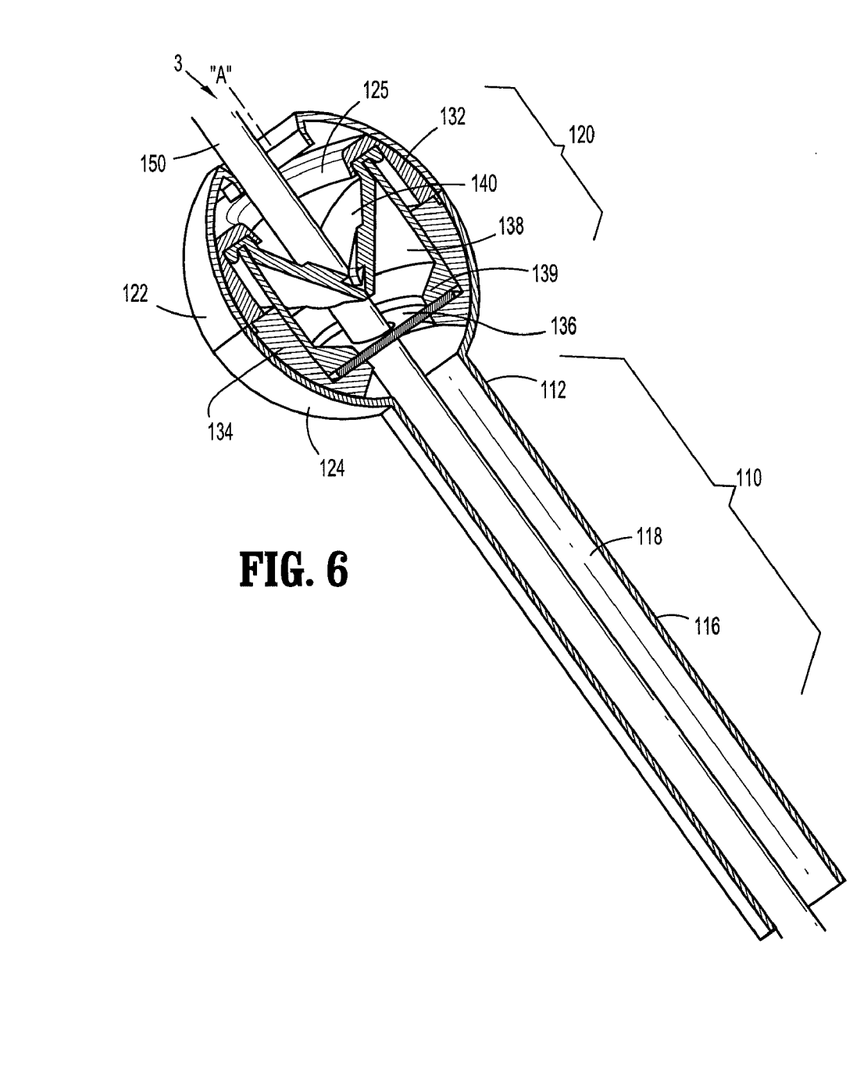
FIG. 6 is a perspective view in cross-section of the portal apparatus of FIG. 5.
Figure 7:
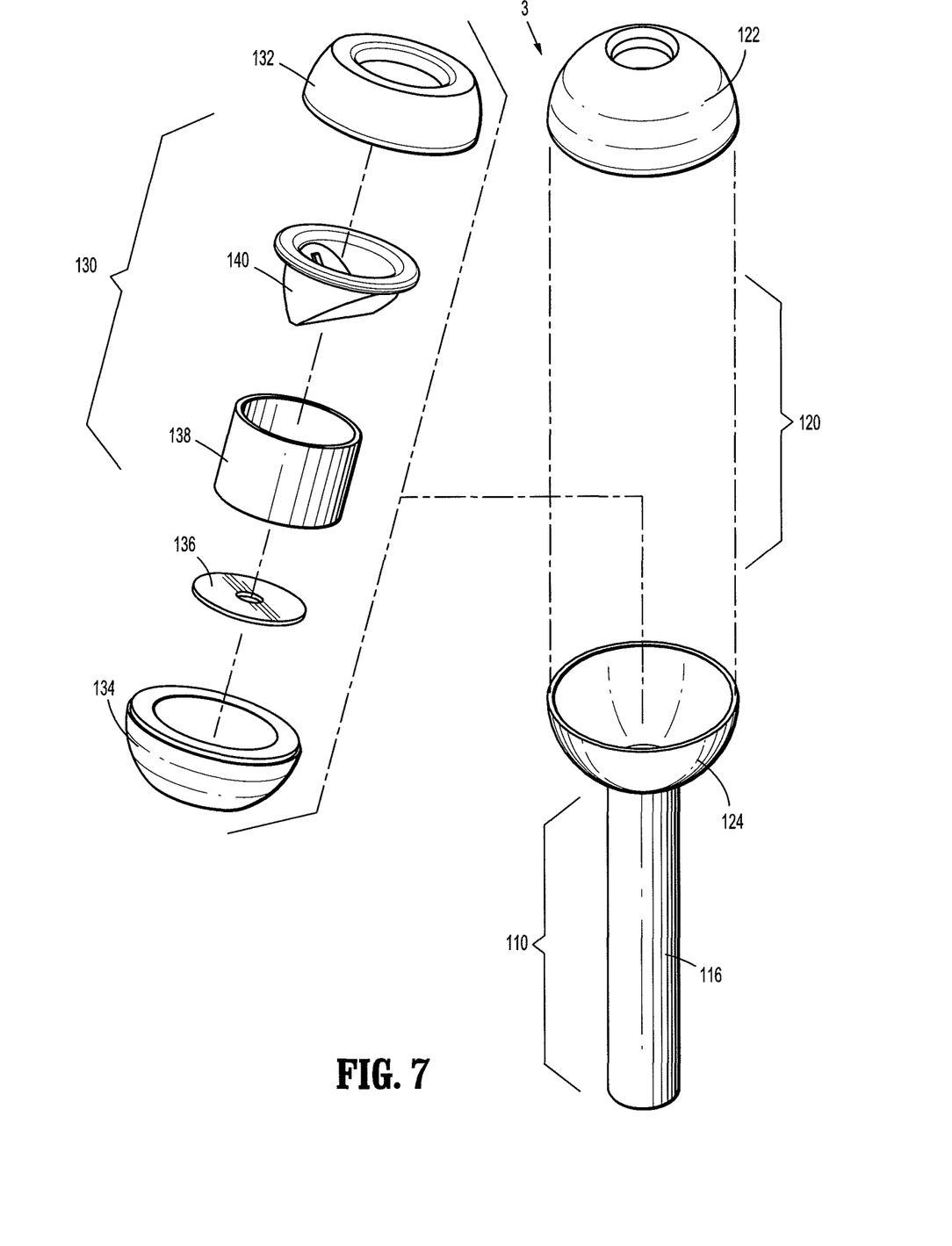
FIG. 7 is a perspective view with parts separated of the portal apparatus of FIG. 5.

FIGS. 5-7 illustrate another embodiment of the present disclosure. With particular reference to FIG. 5, portal apparatus 3 is shown including portal member 110, which may be constructed in a substantially cylindrical shape. Further, portal member 110 includes a portal sleeve 116, having a proximal and distal end 112,114. Portal apparatus 3 further includes a seal housing 120, having a proximal housing component 122 and a distal housing component 124, which is coupled to the proximal end 112 of portal sleeve 116. Seal housing 120 and seal mount 130 further define longitudinal opening 125. During a surgical operation, a user may insert a surgical instrument 150 through opening 125 and into portal apparatus 3.

FIG. 6 is a perspective view in cross-section of the portal apparatus 3. Seal housing 120 includes a seal mount 130 having proximal and distal seal mount components 132 and 134. Also contained within seal housing 120 are a zero closure valve 140 and a mount base 138. In the present configuration, zero closure valve 140 may be mounted on the proximal end of mount base 138. The distal end of mount base 138 may include an inner flange 139 which may rest on object seal 136. Inner flange 139 is tapered to assist in generally directing the surgical object 150 toward the object seal 136 and in general alignment with the longitudinal axis "a", along the internal longitudinal passageway 118 within portal sleeve 116. The aforementioned valve and sealing component(s) may be contained within seal mount 130 which is able to spherically rotate within the inner housing of seal housing 120 thus allowing the user to manipulate instrument/object 150 in multiple positions and angles.

Figure 8:
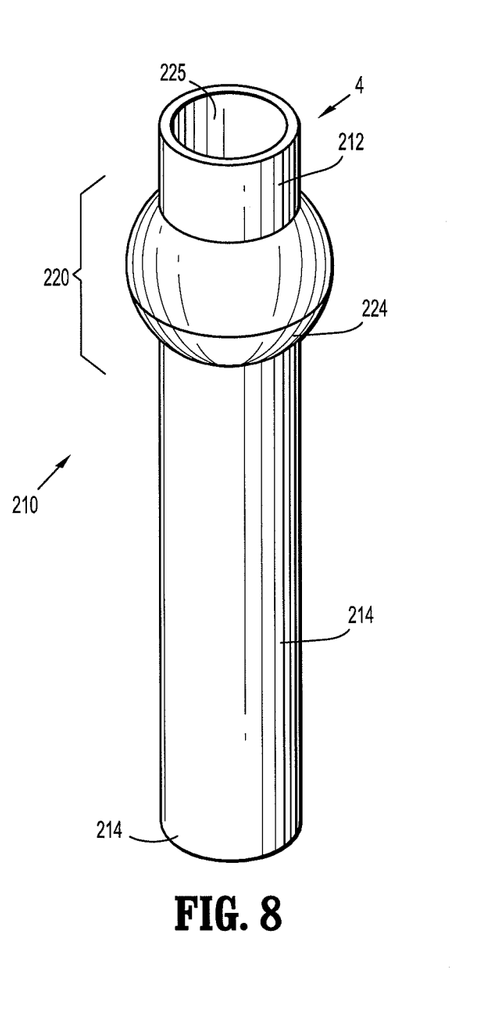
FIG. 8 is a perspective view of an alternate embodiment of the portal apparatus of FIG. 1.
Figure 9:
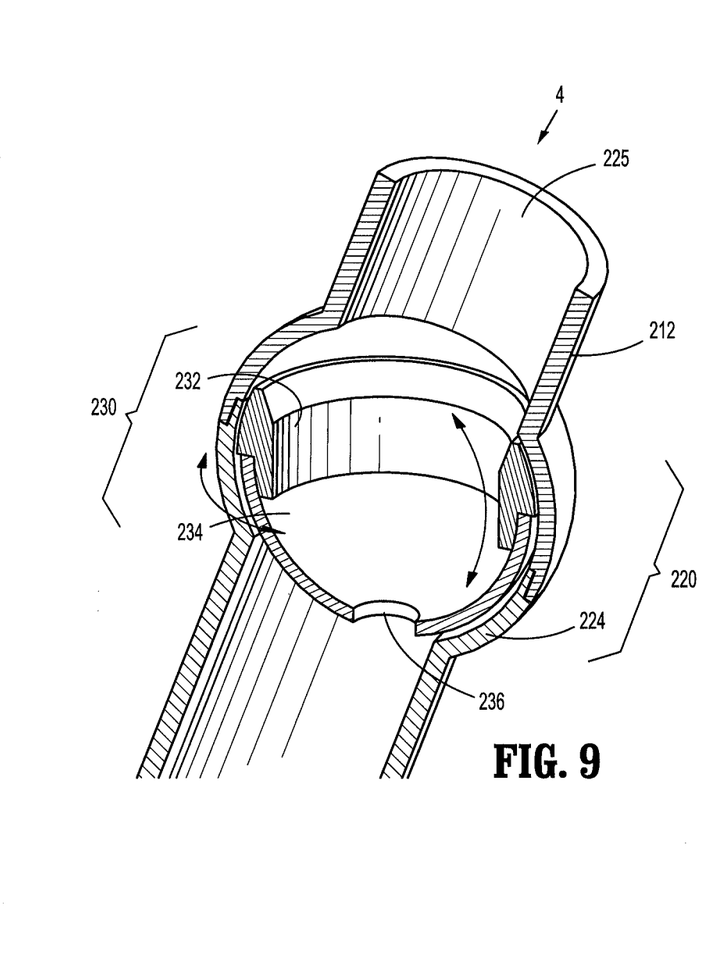
FIG. 9 is a perspective view in cross-section of the seal housing of the portal apparatus of FIG. 8.
Figure 10:
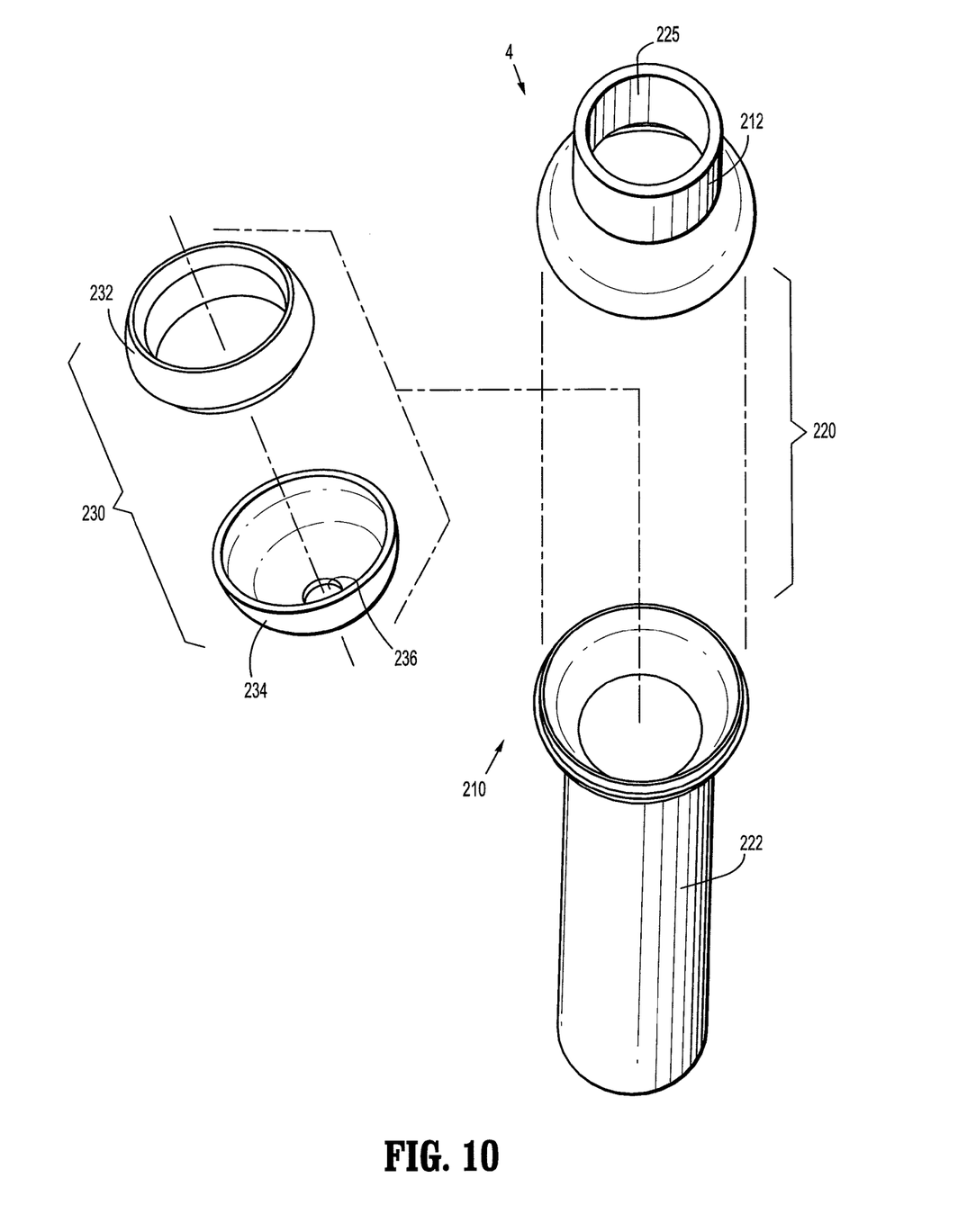
FIG. 10 is a perspective view with parts separated of the portal apparatus of FIG. 8.

Referring now to FIGS. 8-10, portal apparatus 4 in accordance with another embodiment of the present disclosure is illustrated. Portal apparatus 4 includes portal member 210, seal housing 220, and seal mount 230. Seal housing 220 is disposed at an intermediate position of portal member 210, and may be integrally formed with the portal member 210. In one embodiment, portal member 210 includes proximal end segment 212 which is selectively coupled (e.g., screw type connection, snap-fit connection, etc.) or joined permanently (e.g., welded, formed, etc.) to the distal end segment 222 of the portal member 210. Proximal and distal end segments 212,222 define seal housing 220. The positioning of seal housing 220 at an intermediate location of portal member 210 may restrict or limit the degree of angulating movement of the instrument due to the internal constraints of the portal member 210. This may minimize deformation of the object seal within seal mount 230 during offset or angular movement of the instrument, which, may consequently minimize insufflation gas leakage about the instrument. Seal mount 230 includes mount element 232 and object seal 234. Object seal 234 defines a semi-hemispherical configuration which may assist in directing the surgical object through aperture 236 of the object seal 234.

Figure 11:
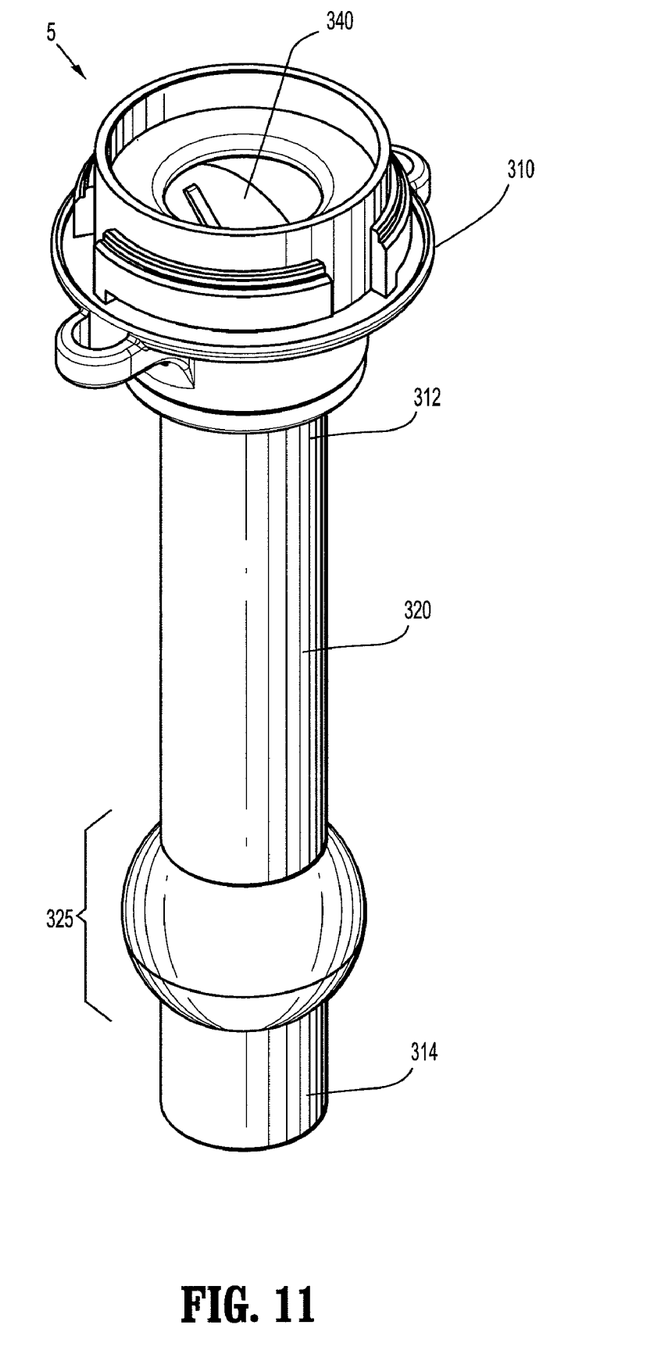
FIG. 11 is a perspective view of an alternate embodiment of the portal apparatus.
Figure 12:
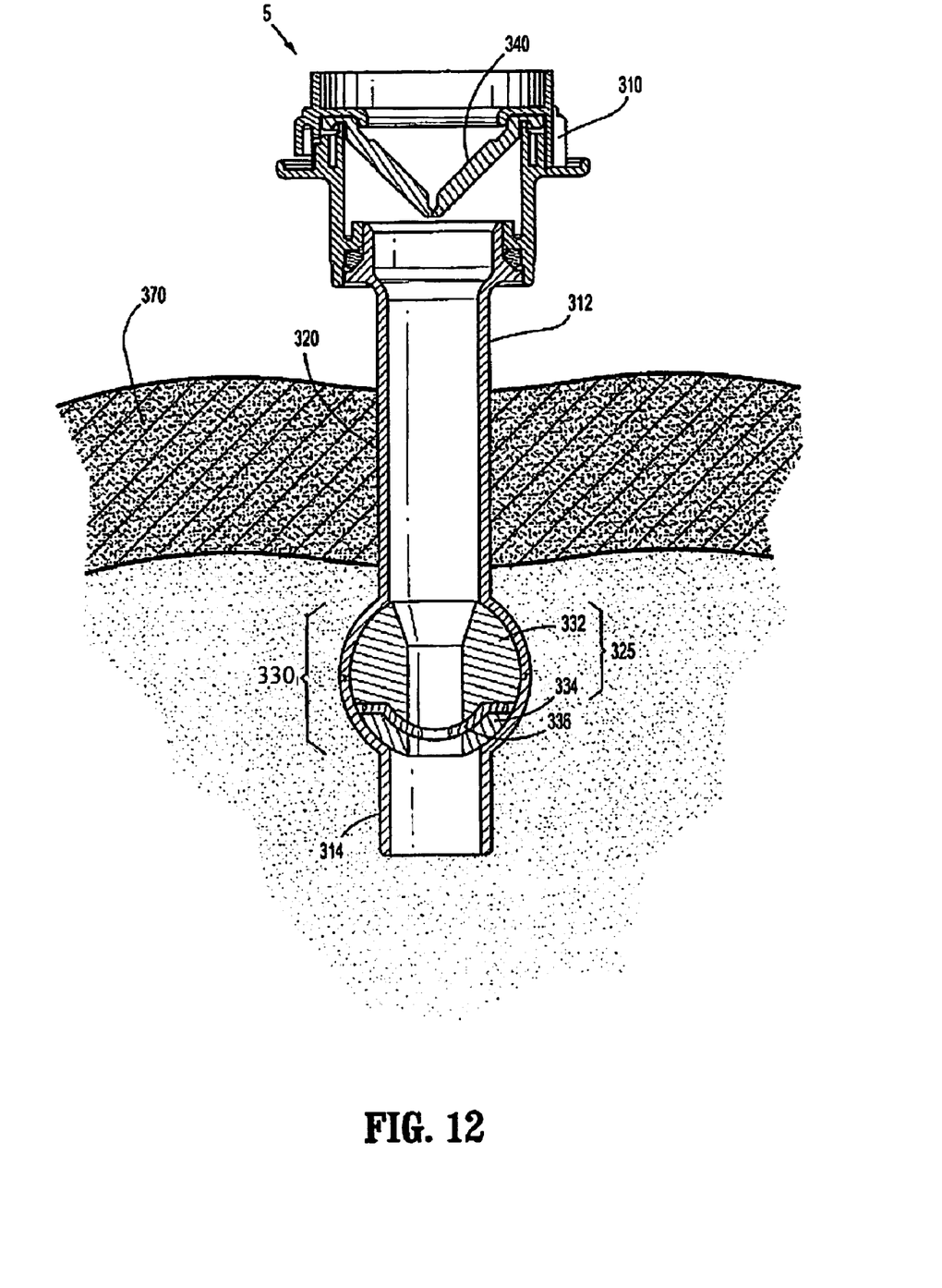
FIG. 12 is a side cross-sectional view of the portal apparatus of FIG. 11 accessing body tissue.

Referring now to FIGS. 11-12, an alternate portal apparatus 5 of the present disclosure is illustrated. Portal apparatus 5 includes valve housing 310 and portal sleeve 320 extending from the valve housing 310. Valve housing 310 includes zero-closure valve 340. Portal sleeve 320 defines seal housing 325 adjacent its distal end, e.g., at an intermediate position between the proximal and distal ends 312, 314 of the portal sleeve 320. Seal housing 325 defines a portal anchor which assists in retaining portal sleeve 320 within tissue. Seal housing 325 includes seal mount 330 contained therein and having proximal and distal mount components 332, 334, and object seal 336 secured between the mount components 332, 334. Object seal 336 creates a sufficient seal about an object. Object seal 336 defines an arcuate contour. The arcuate contour may assist in funneling the instrument through the aperture of object seal 336. The portal anchor defined by seal housing 325 may be generally bulbous in configuration as shown in the illustrations. The bulbous configuration is useful in that it assists in maintaining portal sleeve 320 within the body tissue 370 by minimizing the potential of inadvertent removal or retropulsion of the sleeve 320 relative to the tissue.

Figure 13:
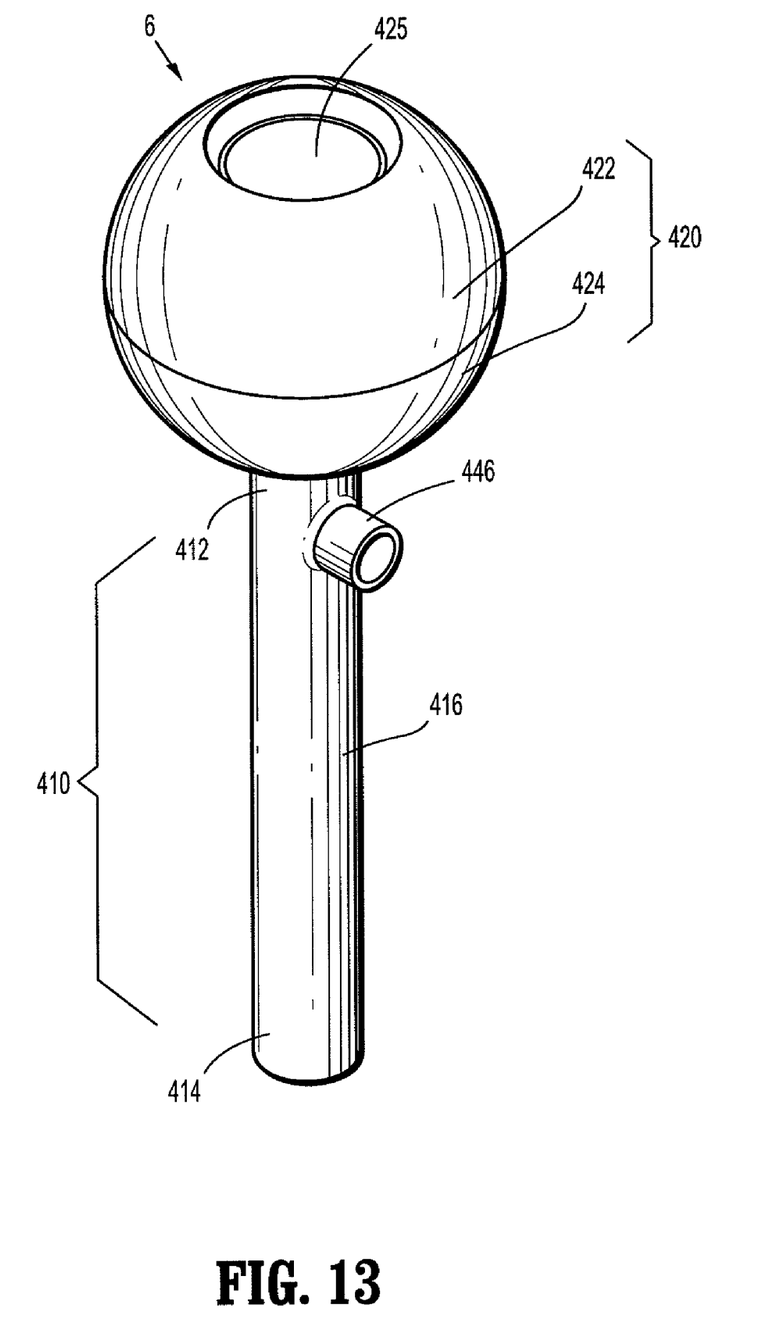
FIG. 13 is a perspective view of another embodiment of the portal apparatus of FIG. 1.
Figure 14:
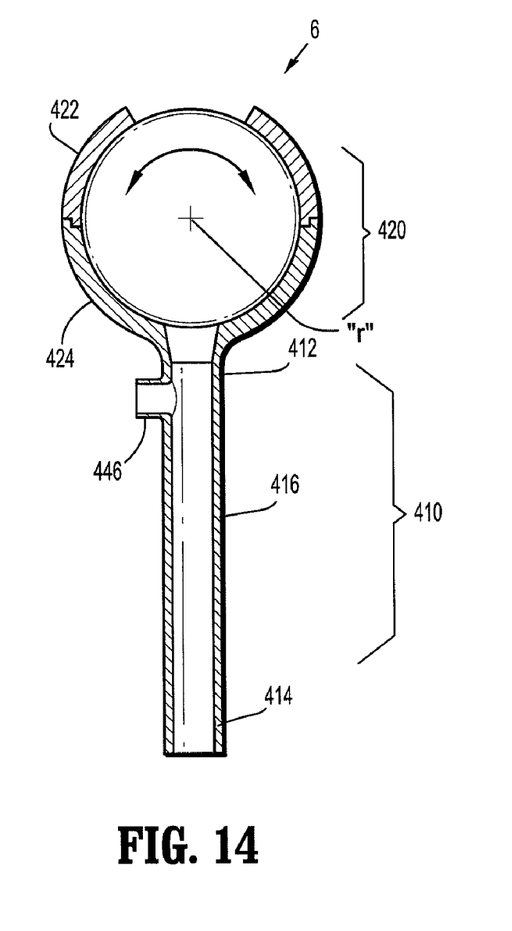
FIG. 14 is a side cross-sectional view of the portal apparatus of FIG. 13.
Figure 15:
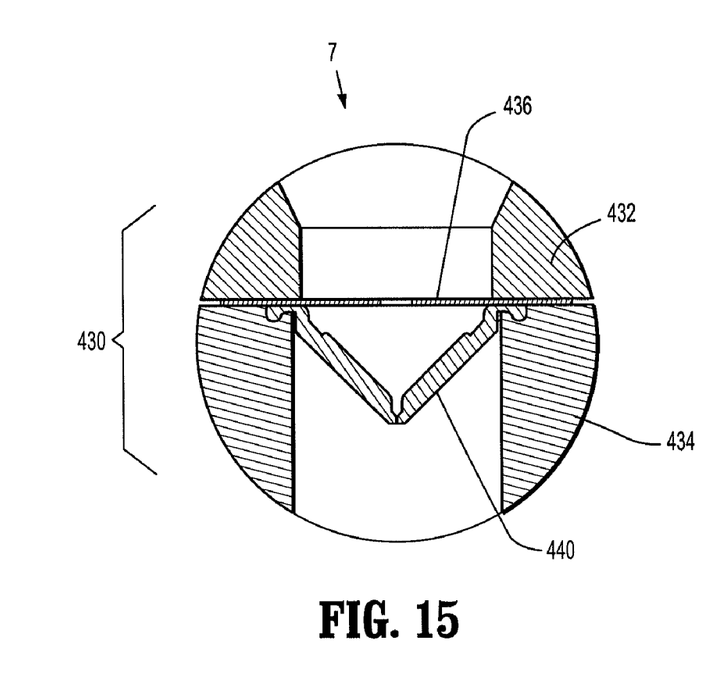
FIG. 15 is a side cross-sectional view of the object seal and the zero-closure valve of the portal apparatus of FIG. 13.

FIGS. 13-15 depict another embodiment of the portal apparatus 6. Portal apparatus includes portal member 410, seal housing 420, and portal sleeve 416, having proximal and distal ends 412 and 414. A stop valve 446 may be incorporated within portal member 410. A suitable valve for this purpose is available from the Burron OEM Division of B. Broun Medical, Inc. (Model No. 55401022). Seal housing 420 contains seal mount 430 which is adapted to rotate about a fixed reference point of rotation "r". During operation, a user may insert a surgical instrument and angulate the seal mount 430 to a specific angle to perform the surgery task. It is envisioned that a locking mechanism (not shown) may selectively lock seal mount at desired predetermined angle orientations with respect to seal housing 420. FIG. 15 is a side cross-sectional view illustrating seal mount 430. Seal mount 430 includes proximal and distal seal mounts 432, 434. In this configuration, object seal 436 is mounted adjacent zero closure valve 440, e.g., in contacting relation therewith. This arrangement may minimize the overall length or profile of seal mount 430 disposed above the operative site.

Figure 16:
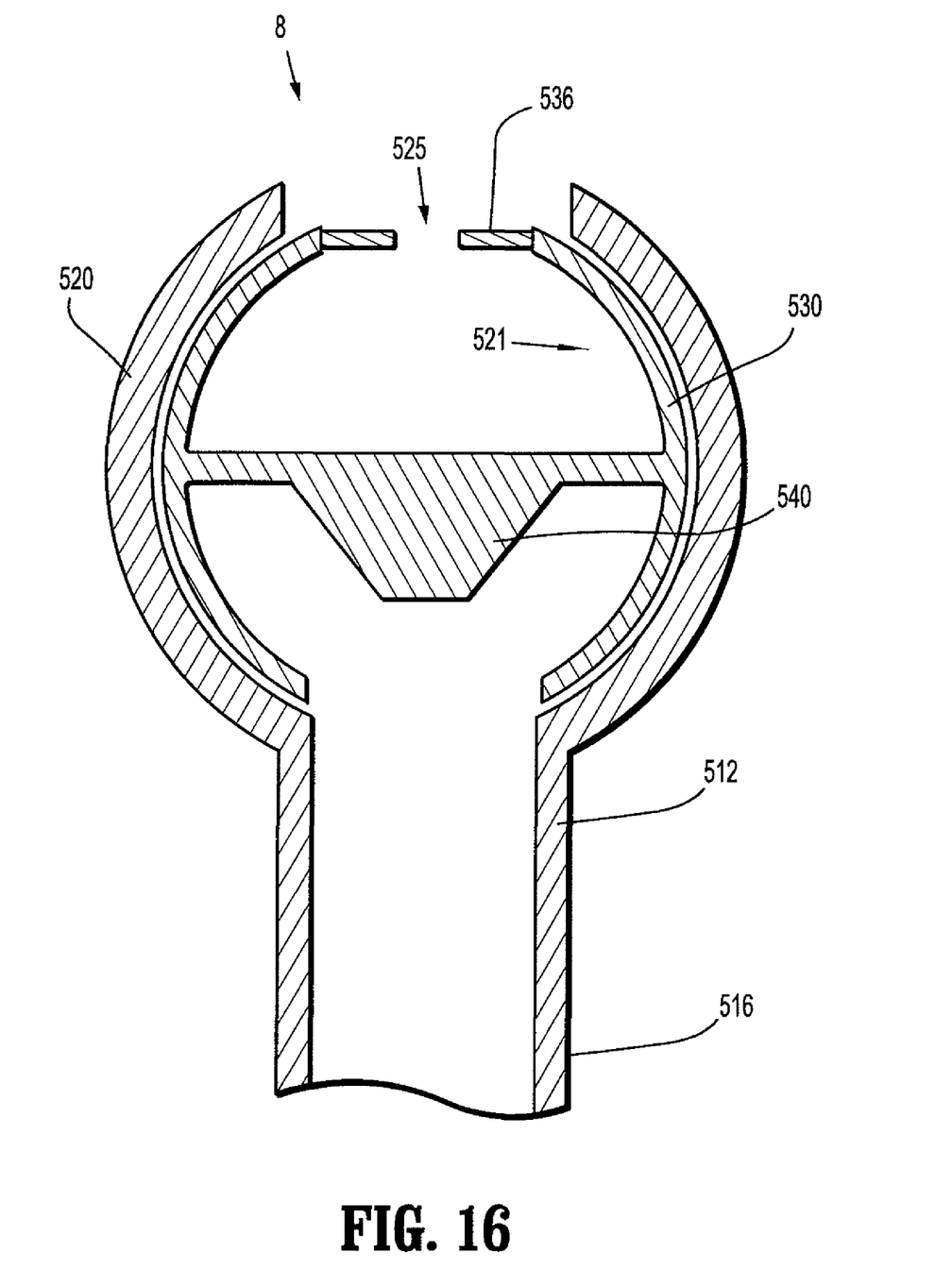
FIG. 16 is a side cross-section view of a further embodiment of the portal apparatus of FIG. 1.

FIG. 16 illustrates a side cross-sectional view of another embodiment of portal apparatus 8. Portal apparatus 8 includes a seal housing 520 mounted on the proximal end 512 of portal sleeve 516. Portal apparatus 8 further includes seal mount 530 having an integrally formed object seal 536, and closure valve 540. In one embodiment, seal mount 530, object seal 536 and closure valve 540 are monolithically formed as a single unit. The monolithically formed mount 530 with seal 536 and valve 540 is disposed within the substantially spherical internal area of seal housing 520. It is envisioned that any one of the components mentioned above may be included in the monolithically formed seal mount, while it is not necessary to include all of them together. Seal mount 530 may be constructed from an elastomeric material or any material contemplated in the art. Seal mount 530 may include a anti-friction coating to facilitate rotation or angulation of the seal mount 530 within seal housing 520.

While the invention has been particularly shown, and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A surgical portal apparatus, which comprises:
   a portal member dimensioned to access tissue and defining a longitudinal axis, and having proximal and distal ends, the portal member having a longitudinal passageway extending from the proximal end to the distal end to permit access to underlying tissue, the portal member having a seal housing disposed between the proximal and the distal ends, the seal housing defining a portal anchor, the portal anchor being positionable within the underlying tissue and being dimensioned and configured to facilitate retention of the portal member within the underlying tissue ; and
   a seal mount at least partially disposed within the seal housing and adapted for spherical rotational movement within the seal housing, the seal mount including an object seal adapted to establish a substantial sealed relation with a surgical object introduced within the longitudinal passageway.

2. The surgical portal apparatus according to claim 1 wherein the seal mount includes a mount base, the object seal being mounted to the mount base.

3. The surgical portal apparatus according to claim 2 wherein the mount base defines an internal taper adapted to generally direct the surgical object toward the object seal and in general alignment with the longitudinal axis.

4. The surgical portal apparatus according to claim 1 wherein the seal mount is adapted to rotate about a fixed reference point of rotation.

5. The surgical portal apparatus according to claim 1 wherein the portal anchor defines a generally bulbous configuration.

6. The surgical portal apparatus according to claim 1 wherein the portal anchor is adjacent the distal end of the portal member.

7. The surgical portal apparatus according to claim 1 including a valve housing mounted to the proximal end of the portal member.

8. The surgical portal apparatus according to claim 7 including a closure valve mounted within the valve housing, the closure valve adapted to substantially close the longitudinal passageway in the absence of the object.

9. The surgical portal apparatus according to claim 1 wherein the portal anchor defines an enlarged dimension relative to portions of the portal member adjacent the portal anchor.

* * * * *

UNITED STATES PATENT AND TRADEMARK OFFICE
CERTIFICATE OF CORRECTION

| | | |
|---|---|---|
| PATENT NO. | : 8,118,783 B2 | Page 1 of 1 |
| APPLICATION NO. | : 12/332391 | |
| DATED | : February 21, 2012 | |
| INVENTOR(S) | : Smith | |

It is certified that error appears in the above-identified patent and that said Letters Patent is hereby corrected as shown below:

Column 1, Cross Reference To Related Application paragraph, incorrectly states the Provisional Application (U.S. Provisional Serial No. 61/024,599) filing date.

The correct filing date U.S. Provisional Serial No. 61/024,599 is:   Jan 30, 2008

Signed and Sealed this
Third Day of April, 2012

David J. Kappos
*Director of the United States Patent and Trademark Office*